United States Patent [19]

Nakamura et al.

[11] Patent Number: 4,496,656
[45] Date of Patent: Jan. 29, 1985

[54] PROCESS FOR PRODUCTION OF CELLULASE

[75] Inventors: Katsumi Nakamura, Takasaki; Kumpei Kitamura, Yoshioka, both of Japan

[73] Assignee: Kirin Beer Kabushiki Kaisha, Tokyo, Japan

[21] Appl. No.: 439,131

[22] Filed: Nov. 4, 1982

[30] Foreign Application Priority Data

Nov. 10, 1981 [JP] Japan .................................. 56-180133

[51] Int. Cl.³ .......................... C12N 9/42; C12N 1/20; C12R 1/01
[52] U.S. Cl. .................................... 435/209; 435/253; 435/822
[58] Field of Search ................................ 435/209, 253

[56] References Cited

U.S. PATENT DOCUMENTS 4,062,727 12/1977 Srinivasan et al. ............. 435/209 X

OTHER PUBLICATIONS

American Type Culture Catalogue of Strains I, 15th Edition, 1982, p. 93.

Primary Examiner—Lionel M. Shapiro
Attorney, Agent, or Firm—Ladas & Parry

[57] ABSTRACT

A novel bacterium, *Cellulomonas uda* CB4, and production of cellulase by cultivation of the bacterium on a medium containing a cellulosic material are disclosed.

6 Claims, 3 Drawing Figures

FIG. I

PROCESS FOR PRODUCTION OF CELLULASE

BACKGROUND OF THE INVENTION

This invention relates to a process for production of cellulase by utilizing bacteria.

In recent years, attempts have been made to convert cellulose resources into sugars with the use of enzymes on a scale of a national project as one of the developments of biomass energy.

As an enzyme suitable for such a purpose, it is preferred to use cellulase having a high activity for decomposition of crystalline celluloses. As such a cellulase, those produced by microorganisms belonging to a mold such as Trichoderma, Irpex, Aspergillus, and Sporotrichum are well known in the art. However, a long term (one to two weeks) is necessary for production of cellulase by the culturing of a mold. As another drawback, solid culturing is preferred for a mold.

On the other hand, among bacteria, Cellulomonas has been well known in the art as cellulase-producing microorganism, but it has been reported that the cellulases produced therefrom are noticeably low in activity of decomposing crystalline cellulose and also that the enzyme related to crystalline cellulose decomposition is not excreted out of the microorganism cells [Aust. J. Biol. Sci., Vol. 31, pp. 553–564 (1978)]. Therefore, concerning production of cellulase, no practical development comparable to those with the use of molds has yet been reported in the case of bacteria.

SUMMARY OF THE INVENTION

This invention has been accomplished on the basis of the finding, as the result of extensive studies made with an object to produce a cellulase comparable to those from a mold with the use of a bacterium, that said object can be achieved by employment of a bacterium belonging to *Cellulomonas uda* CB4.

Accordingly, the present invention is concerned with a novel bacterium which is *Cellulomonas uda* CB4 or its mutant.

The process for production of cellulase according to the present invention thus comprises culturing a cellulase-producing microorganism belonging to *Cellulomonas uda* CB4 in a cellulose-containing medium, and recovering the cellulase produced from the culture broth.

According to the present invention, because the bacteria belonging to *Cellulomonas uda* CB4 is capable of producing a cellulase having a high activity, not found in the reports of the prior art, in a culture medium, it is possible to produce a cellulase having a high crystalline cellulose decomposing activity comparable to those produced from a mold within a short cultivation period of two days.

The nature, utility, and further features of this invention will be more clearly apparent from the following detailed description, beginning with a consideration of general aspects of the invention and concluding with specific examples of practice thereof, when read in conjunction with the accompanying drawing, briefly described below.

DETAILED DESCRIPTION OF THE INVENTION

1. CELLULASE-PRODUCING MICROORGANISM

Figure 1:
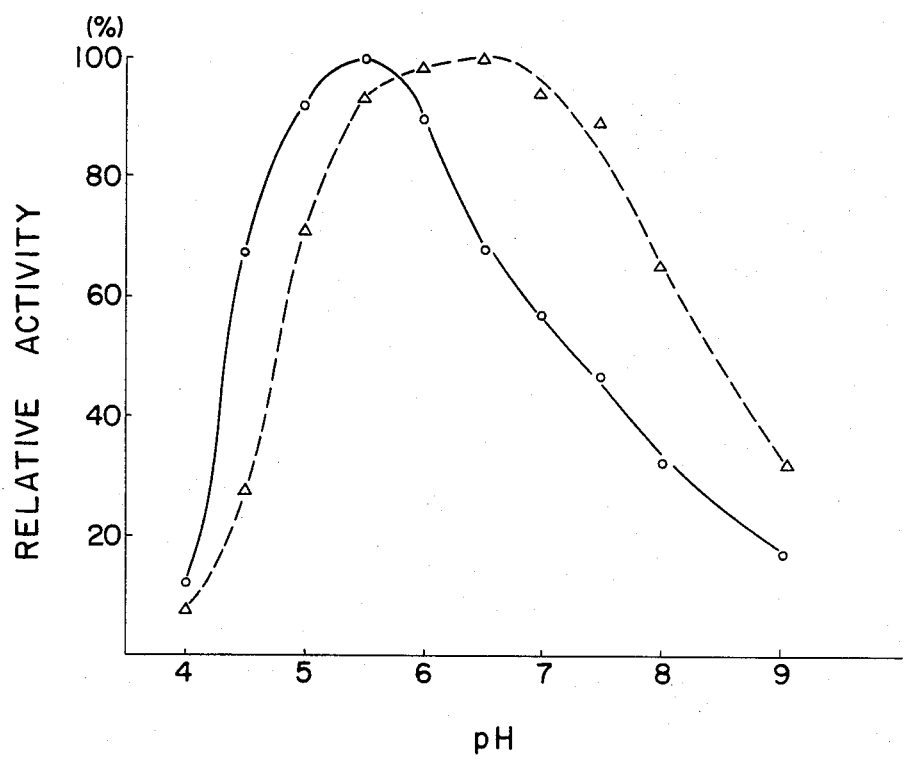
FIGS. 1, 2, and 3 are graphs, indicating the relative activity of the cellulase obtained by this invention in relation to the acting pH (FIG. 1), the acting temperature (FIG. 2) and the storage temperature (FIG. 3). In the drawings, the solid line shows the results when the substrate cellulose is Avicel and the dotted line those when it is CMC.

The cellulase-producing microorganism to be used in the present invention is a bacterium belonging to *Cellulomonas uda* CB4.

The term "a bacterium belonging to *Cellulomonas uda* CB4" herein means a bacterium derived from the strain *Cellulomonas uda* CB4 through mutation thereof by, for example, high energy irradiation. *Cellulomonas uda* CB4 and its mutants are thus hereby disclosed.

A typical example of such a bacterium is a name strain *Cellulomonas uda* CB4.

*Cellulomonas uda* CB4 was isolated after enrichment culture of brewery sewage in a beer factory in Takasaki City, Japan, and has the following bacteriological properties:

(1) Morphological properties
  Shape: irregular rods
  Size: $0.4 \times 0.8 - 4.8\mu$
  Motility: negative
  Gram-stain: positive
  Culture morphology: good growth in bouillon agar plate culture, smooth surface, clearly brimmed, yellow color, and viscous nature.
(2) Physiological properties
  Growth temperature: 16°–38° C.
  Growth pH: 6.0–10.6
  Oxygen requirement: facultative anaerobic
  Catalase reaction: positive
  Nitrate reduction: positive
  Gelatin liquefaction: slowly liquefied
  Acetylmethylcarbinol production: negative
  Methyl red test: positive
  Diastase production: positive
  Vitamin requirement: biotin, thiamine
  Utilization of inorganic nitrogen: positive
  Decomposition of filter paper: positive
  Acid formation from glucose: positive
  Ammonia formation from peptone: positive
  Assimilation of ribose, raffinose: negative
  Assimilation of acetate: positive
  Assimilation of L(+)-lactate, gluconate: negative
  Type of peptideglucan of cell wall: L-Orn-D-Glu
  Sugar composition of cell wall polysaccharides: mainly glucose and trace amounts of ribose, mannose From the bacteriological properties as described above, the present microorganism is determined from the "Bergey's Manual of Determinative Bacteriology, 8th Ed. (1974)" and "International Journal of Systematic Bacteriology, Vol. 29, pp. 273–282 (1979)" as belonging to *Cellulomonas uda*. However, the present microorganism is greatly different from the known *Cellulomonas uda* in cellulase producing ability, and hence the present microorganism was named *Cellulomonas uda* CB4.

*Cellulomonas uda* CB4 is deposited at Fermentation Research Institute, Agency of Industrial Science & Technology, 1-3, Higashi 1-chome, Yatabe-machi, Tsukuba-gun, Ibaraki-ken 305, Japan, as FERM BP-199

(Sept. 7, 1981) under the BUDAPEST TREATY ON THE INTERNATIONAL RECOGNITION OF THE DEPOSIT OF MICROORGANISMS FOR THE PURPOSES OF PATENT PROCEDURE.

Table 1 shows the differences in cellulase-producing ability between the present microorganism and the known bacteria of the genus Cellulomonas including *Cellulomonas uda*. Cellulase activity was determined by inoculating each strain in a cultural medium comprising 2% Avicel, 2% polypeptone, 0.2% $K_2HPO_4$, 0.05% $MgSO_4.7H_2O$, 0.05% yeast extract and 0.1% Tween 80 (trade mark), carrying out shaking cultivation at 30° C. for two days, subjecting the culture broth to centrifugation and analyzing the supernatant obtained.

TABLE 1

| Microorganism strain | Cellulase activity (unit/ml) | | |
|---|---|---|---|
| | Avicel decomposing activity (1) | Filter paper decomposing activity (2) | CMC decomposing activity (3) |
| *C. uda* CB4 | 0.92 | 0.38 | 31.68 |
| *C. uda* ATCC 491 | 0.08 | 0.06 | 1.38 |
| *C. flavigena* ATCC 482 | 0 | 0 | 0.43 |
| *C. gelida* ATCC 488 | 0.07 | 0.05 | 1.87 |
| *C. cartae* ATCC 21681 | 0.07 | 0.08 | 6.95 |
| *C. fimi* ATCC 484 | 0 | 0 | 0 |
| *C. cellasea* ATCC 487 | 0 | 0 | 0 |
| *C. biazotea* ATCC 486 | 0 | 0.02 | 0.20 |
| Reference example *Trichoderma reesei* QM 9414 | 0.40 (4) | 1.48 (5) | 1.52 (5) |

(1) Avicel decomposing activity:

A mixture of 2.0 ml of an acetate buffer of pH 5.5 containing 1% Avicel (produced by Merck Co.) and 0.2 ml of an enzyme solution was subjected to the reaction at 45° C. for one hour, maintained in a boiling water bath for 5 minutes to stop the reaction, and the reaction mixture was filtered with a filter paper. The amount of the reducing sugar in the filtrate was determined quantitatively as glucose according to the dinitrosalicylic acid method.

(2) Filter paper decomposing activity:

Following the procedure of Mandels et al [J. Ferment. Technol., Vol. 54, p. 267–286 (1976)], 0.5 ml of an enzyme solution was added into 1 ml of an acetate buffer of pH 5.5, a filter paper of 1×6-cm size was added into the mixture, which was then mixed, and the reaction was carried out at 45° C. for one hour. The amount of the reducing sugar liberated in the reaction mixture was determined quantitatively as glucose according to the dinitrosalicylic acid method.

(3) CMC decomposing activity:

To 2 ml of an acetate buffer of pH 5.5 containing 1% carboxymethyl cellulose (produced by Sigma Co.) was added 0.1 ml of an enzyme solution. Then the reaction was carried out at 45° C. for 10 minutes, and the amount of reducing sugar liberated was determined quantitatively as glucose according to the dinitrosalicylic acid method.

In each of the above activity measurement methods, the amount of enzyme which can liberate a reducing sugar corresponding to one micromole of glucose per one minute was determined as one unit.

(4) M. Desrochers, et al., Appl. Environ. Microbiol., Vol. 41, p.222 (1981)

(5) M. Mandels, et al., Biotechnol. Bioeng., Vol. 16, p.1471 (1974).

*Cellulomonas uda* CB4, as compared with the known *Cellulonomas uda* ATCC 491, can produce an Avicel decomposing activity higher by 16-fold or more, a filter paper decomposing activity higher by 5-fold or more and a CMC decomposing activity higher by 20-fold or more, thus being clearly distinguished from the known *Cellullomonas uda*. *Cellulomonas uda* CB4 can also produce markedly higher cellulase activity than other bacteria of the genus Cellulomonas, indicating that the present microorganism is a specific bacterium not known in the prior art. Further, the present microorganism can also produce an activity for Avicel decomposition higher than the literature value of *Trichoderma reesei* QM 9414 which is at present deemed to produce the highest cellulase activity.

2. PRODUCTION OF CELLULASE

Production of cellulase is carried out by culturing a bacterium belonging to *Cellulomonas uda* CB4 in a medium containing cellulose.

As the carbon source to be utilized in the production, various cellulosic materials can be employed as a single species or in combinations. More specifically, examples of such materials are: natural cellulose such as cotton, cotton threads, absorbent or defatted cotton, sawdust, soybean tailing, etc.; chemically treated cellulose such as general papers, filter paper, pulp, etc.; regenerated cellulose such as Cellophane, Avicel, etc.; and cellulose derivatives such as carboxymethyl cellulose and hydroxyethyl cellulose. As the nitrogen source, inorganic ammonium salts such as ammonium sulfate, ammonium nitrate, etc. and organic nitrogen sources such as urea, amino acid, meat extract, yeast extract, polypeptone, and proteolytic products are employed. In addition, it is also possible to use an ordinary medium containing inorganic salts such as $K_2HPO_4$, and $MgSO_4$, or, if necessary, organic trace nutrients such as vitamins or surfactants such as Tween 80 (trade mark). Cultivation is carried out by way of liquid cultivation, and a conventional culturing device under aerating agitation is employed therefor. The cultivation temperature is 20° to 38° C., preferably 23° to 31° C., and the cultivation pH is pH 6.5 to 9.0, preferably around pH 8.0. The cultivation time is generally 2 to 3 days.

Recovery of the cellulase produced can be conducted according to a conventional procedure. More specifically, the culture broth obtained after the treatment for removal of microorganism cells such as centrifugation or filtration can be used as such as a crude enzyme solution. Further, a crude enzyme agent can be obtained according to a known method such as salting-out with ammonium sulfate or precipitation with an organic solvent.

3. CELLULASE PRODUCED

*Cellulomonas uda* CB4 strain was cultured as described above, and the cultural supernatant obtained was examined with respect to various properties to obtain the following results.

(1) Substrate and decomposition products

A natural cellulose such as cotton, cotton threads, absorbent or defatted cotton, sanddust, soybean tailing, or beer tailing; chemically treated cellulose such as general papers, filter paper, or pulp; regenerated cellulose such as Cellophane or Avicel; or cellulose derivative such as carboxymethyl cellulose (CMC), or HE-cellulose, can be hydrolyzed to produce mainly cellobiose and a trace amount of glucose. The cellulase of the present invention is an enzyme complex similarly as the known cellulases, but it is weaker in $\beta$-glucosidase activity and the main decomposition product is cellobiose.

(2) Optimum acting pH and pH stability

As shown in FIG. 1, the optimum acting pH for Avicel decomposing activity (represented by the solid line) is pH 5.5, while it is pH 6.5 for CMC decomposing activity (represented by the dotted line). The stable pH region when left to stand at 25° C. for 24 hours is pH 5 to 8 for both Avicel and CMC decomposing activities.

(3) Optimum acting temperature and heat stability

Figure 2:
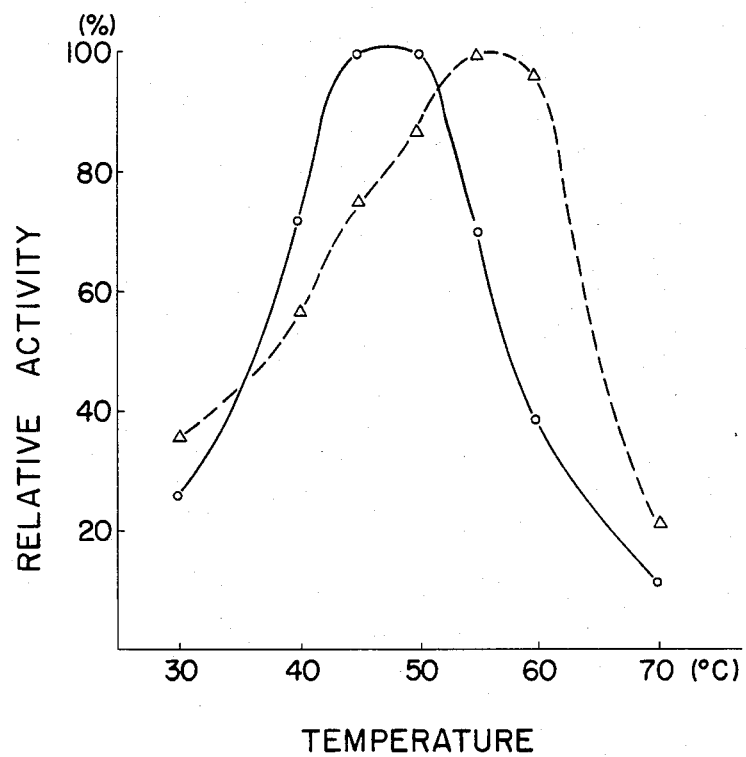
Figure 3:
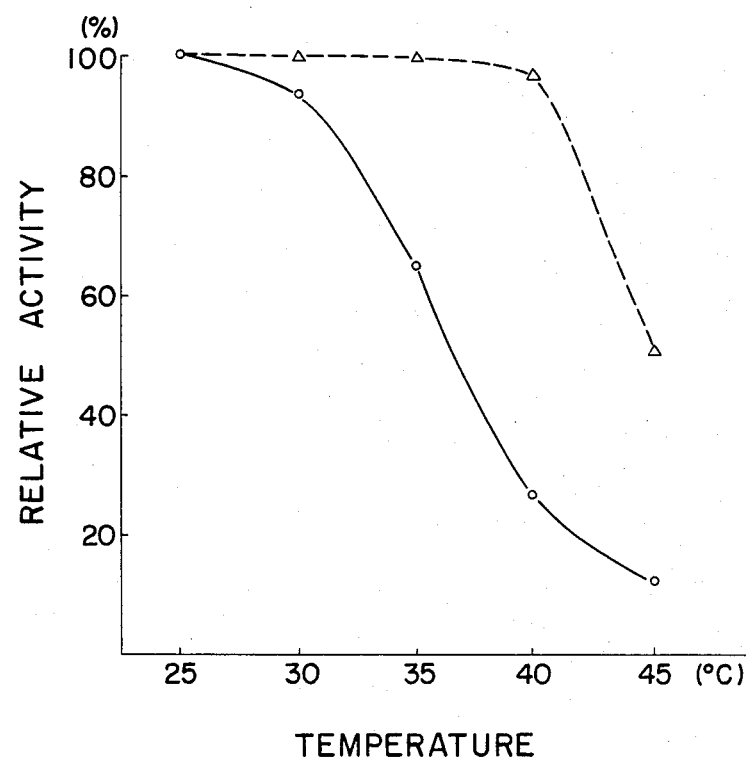

As shown in FIG. 2, the optimum acting temperature for Avicel decomposing activity (represented by the solid line) is 45° to 50° C., while it is 55° C. for CMC decomposing activity (represented by the dotted line). Also, as shown in FIG. 3, the heat stability when left to stand under various temperature conditions for 24 hours in an acetate buffer of pH 5.5 was higher in case of CMC decomposing activity (represented by the dotted line) than in case of Avicel decomposing activity (represented by the solid line). That is, when left to stand at 40° C. for 24 hours, CMC decomposing activity remains to be 100%, while Avicel decomposing activity is lost by about 70%.

(4) Activators and inhibitors

Avicel decomposing activity can be activated to 1.5- to 2.5-fold by 1 mM $MnCl_2$, $CoCl_2$ and 10 mM $CaCl_2$, and inhibited by about 70% by 1 mM SDS (sodium dodecyl sulfate) and 10 mM CTAB (cetyltrimethylammonium bromide), $CuCl_2$.

CMC decomposing activity can be activated to 1.3-fold by 10 mM $CaCl_2$ and 1 mM $FeSO_4$, and inhibited substantially completely by 10 mM $CuCl_2$.

The cellulase activity produced by the molds of the genus Aspergillus and the genus Trichoderma is inhibited by divalent metal ions such as of Mn, Cu, Zn, etc., and the cellulase produced by the mold of the genus Sporotrichum is activated by these divalent metal ions. In contrast, the cellulase of the present invention is activated by Mn, Co and Ca of the divalent metal ions, while it is inhibited by Zn and Cu, as clearly distinguished from the enzymes of the prior art.

4. EXPERIMENTAL EXAMPLES

Example 1

One platinum loop of *Cellulomonas uda* CB4 was inoculated into 10 ml of a meat extract medium, and shaking cultivation was carried out at 30° C. for 2 days to prepare a pre-culture. This pre-culture (0.5 ml) was inoculated into 50 ml of a medium containing Avicel (2% Avicel, 2% polypeptone, 0.2% $K_2HPO_4$, 0.05% $MgSO_4.7H_2O$, 0.05% yeast extract, 0.1% Tween 80, pH 8.0), and shaking cultivation was carried out at 30° C. for 2 days. The culture broth was subjected to centrifugation, and the supernatant obtained was found to exhibit enzyme activities of 1.04 unit/ml for Avicel decomposition and 23.3 unit/ml for CMC decomposition, respectively.

Example 2

To 400 ml of the culture supernatant obtained in Example 1 was added 640 ml of cold acetone, and the resultant precipitate was collected by centrifugation and dried under reduced pressure to produce 1.5 g of a crude enzyme. The sample had an Avicel decomposing activity of 58.2 units/g and a CMC decomposing activity of 2170 units/g.

Example 3

The pre-culture of *Cellulomonas uda* CB4 (0.5 ml) prepared similarly as in Example 1 was inoculated into 50 ml of a medium containing beer tailing (2% beer tailing, 2% polypeptone, 0.2% $K_2HPO_4$, 0.05% $MgSO_4.7H_2O$, 0.05% yeast extract, 0.1% Tween 80, pH 8.0), and shaking cultivation was carried out at 30° C. for 2 days. The supernatant obtained by centrifuging this culture broth was found to exhibit an Avicel decomposing activity of 0.22 unit/ml and a CMC decomposing activity of 5.7 units/ml.

We claim:

1. A process for producing a cellulase, which comprises culturing a cellulase-producing microorganism belonging to *Cellulomonas uda* CB4 in a cellulose-containing medium and recovering the cellulase produced.

2. A process for producing a cellulase according to claim 1, wherein the cellulase-producing microorganism belonging to *Cellulomonas uda* CB4 is selected from the group consisting of *Cellulomonas uda* CB4 (FERM BP-199) and mutants thereof.

3. A process for producing a cellulase according to claim 1, wherein the cellulase-producing microorganism is *Cellulomonas uda* CB4 (FERM BP-199).

4. A biologically pure culture of a bacterium selected from the group consisting of *Cellulomonas uda* CB4 (FERM BP-199) and mutants thereof.

5. A biologically pure culture of a bacterium *Cellulomonas uda* CB4 (FERM BP-199).

6. A bacterium selected from the group consisting essentially of *Cellulomonas uda* CB4 (FERM BP-199) and mutants thereof.

* * * * *